(12) United States Patent
Chiodi

(10) Patent No.: US 6,846,637 B1
(45) Date of Patent: Jan. 25, 2005

(54) FAS PEPTIDES AND ANTIBODIES FOR MODULATING APOPTOSIS

(75) Inventor: Francesca Chiodi, Stockholm (SE)

(73) Assignee: IMED AB, Stockholm (SE)

(*) Notice: Subject to any disclaimer, the term of this patent is extended or adjusted under 35 U.S.C. 154(b) by 0 days.

(21) Appl. No.: 09/719,646

(22) PCT Filed: Jun. 15, 1999

(86) PCT No.: PCT/EP99/04105

§ 371 (c)(1),
(2), (4) Date: Feb. 28, 2001

(87) PCT Pub. No.: WO99/65935

PCT Pub. Date: Dec. 23, 1999

(30) Foreign Application Priority Data

Jun. 18, 1998 (GB) .............................. 9813194
Mar. 12, 1999 (GB) .............................. 9905793

(51) Int. Cl.[7] .......................... C12Q 1/00; G01N 33/53; A61K 39/395; A61K 39/00; A01N 61/00
(52) U.S. Cl. .......................... 435/7.1; 435/4; 424/130.1; 424/140.1; 436/536; 514/1; 514/2; 514/13; 514/15; 530/300; 530/350
(58) Field of Search ................................. 530/300, 350; 514/1, 2, 13, 15; 424/130.1, 140.1; 430/536; 435/4, 7.1

(56) References Cited

U.S. PATENT DOCUMENTS

| 5,620,889 A | 4/1997 | Lynch et al. |
| 5,652,210 A | 7/1997 | Barr et al. |
| 5,663,070 A | 9/1997 | Barr et al. |
| 5,830,469 A | 11/1998 | Lynch et al. |
| 5,874,546 A | 2/1999 | Nagata et al. |
| 5,891,434 A | 4/1999 | Krammer et al. |
| 6,015,559 A | 1/2000 | Lynch et al. |
| 6,086,877 A | 7/2000 | Nishioka et al. |
| 6,270,998 B1 | 8/2001 | Nagata et al. |

FOREIGN PATENT DOCUMENTS

| DE | 195 44 332 A1 | 6/1997 |
| EP | 0 510 691 A1 | 10/1992 |
| EP | 0 511 202 B1 | 11/1992 |
| EP | 0 709 097 A1 | 5/1996 |
| EP | 0 716 095 A1 | 6/1996 |
| EP | 0 799 891 A1 | 10/1997 |
| EP | 0 866 131 A2 | 9/1998 |
| EP | 0 909 816 A1 | 4/1999 |
| EP | 0 990 663 A2 | 4/2000 |
| EP | 1180369 A1 | 2/2002 |
| JP | 09 166593 A | 6/1997 |
| WO | WO 95/10540 | 4/1995 |
| WO | WO 95/13701 | 5/1995 |
| WO | WO 97/12632 | 4/1997 |
| WO | WO 98/08965 | 3/1998 |

OTHER PUBLICATIONS

G.C. Starling et al., "Identification of Amino Acid Residues Important for Ligand Binding to Fas"; J.Exp.Med—Brief Definitive Report, vol. 185, No. 8:1487–1492 (1997).

N. Prasad et al., "Therapeutic Preparations of Normal Polyspecific IgG (IVIg) Induce Apoptosis in Human Lymphocytes and Monocytes: A Novel Mechanism of Action of IVIg Involving the Fas Apoptotic Pathway"; The Journal of Immunology, 3781–3790 (1998).

I. Viard et al., "Inhibition of Toxic Epidermal Necrolysis by Blockade of CD95 with Human Intravenous Immunoglobulin", Science, vol. 282:490–493 (1998).

B. Fadeel et al., "A three–dimensional model of the Fas/APO–1 molecule: cross–reactivity of anti–Fas antibodies explained by structural mimicry of antigenic sites", International Immunology, vol. 10, No. 2:131–140 (1998).

B. Fadeel et al., "Anti–Fas IgG1 antibodies recognizing the same epitope of Fas/APO–1 mediate different biological effects in vitro", International Immunology, vol. 9, No. 2:201–209 (1997).

B. Fadeel et al., "Mapping of the linear site on the Fas/APO–1 molecule targeted by the prototypic anti–Fas mAb". International Immunology, vol. 7, No. 12:1967–1975 (1995).

Stricker, K., et al., "Anti–CD95 (APO–1/Fas) autoantibodies and T cell depletion in human immunodeficiency virus Type 1 (HIV–1)–infected children", Cell Death and Differentiation, 5: 222–230, (1998).

*Primary Examiner*—Alana M. Harris
(74) *Attorney, Agent, or Firm*—Dann, Dorfman, Herrell & Skillman, P.C.

(57) ABSTRACT

Anti-Fas (APO-1, CD95) autoantibodies arm found in human s, which antibodies arm biologically functional. Peptide fragments of Fas recognized by such antibodies, and antibodies specific for such peptides, inhibit or promote apoptosis and cellular proliferation. Assay methods making use of Fas peptides or antibodies enable identification of further agents which modulate apoptosis and/or cellular proliferation.

4 Claims, 4 Drawing Sheets

FAS PEPTIDES AND ANTIBODIES FOR MODULATING APOPTOSIS

The present invention relates in various aspects to methods and means for modulating apoptosis and/or cellular proliferation, in particular via stimulation or inhibition of Fas (also known as APO-1 and CD95). It is based in part on the surprising discovery of anti-Fas autoantibodies in human sera, which antibodies moreover are biologically functional and include both IgG and IgM antibodies. Peptide fragments of Fas and variants and mimetics thereof may be used in modulating apoptosis for therapeutic purposes.

Affinity-purified anti-Fas antibodies isolated from the serum of healthy blood donors have been found by the present inventors to be able to inhibit proliferation and to induce apoptosis of Jurkat leukemia T cells. This effect is inhibited by soluble Fas-Fc chimeric protein. Costimulation of peripheral blood mononuclear cells by human anti-Fas autoantibodies and anti-CD3 monoclonal antibodies induces or inhibits cell proliferation depending on the activation state of the cells. Anti-Pas autoantibodies may thus represent an additional mode of regulation of Fas-mediated signals in vivo which may be harnessed in accordance with the present invention.

Fas (also called CD95/APO-1) is a type I cellular receptor protein, belonging to the nerve growth factor/tumor necrosis factor (NGF/TNF) receptor family (Itoh, et a l., 1991; Smith et al., 1994). The receptor has been shown to transduce an apoptotic signal in various cell types upon binding of its natural ligand, aas ligand (FasL) (Suda et al., 1993).

Certain anti-Fas monoclonal antibodies have also been shown to trigger Fas signaling by crosslinking this receptor in vitro. Anti-Fas antibodies can (i) induce apoptosis of immortalized and chronically stimulated T and B cells (Yonehara et al., 1989; Trauth et al., 1989; Weis et al., 1995; Mapara et al., 1993; Owen-Schaub et al., 1992; Kias et al., 1993) and liver cells (Ogasawara et al., 1993); (ii) induce proliferation of peripheral lymphocytes in response to anti-CD3 antibody (Alderson et al., 1993; Alderson et al, 1994); (iii) inhibit apoptosis induced by either another anti-Fas antibody (Silvestris et al., 1996) or FasL (Alderson et al, 1994). Fas has been suggested to play a major role in organ-specific destruction during autoimmune conditions and infectious diseases (Katsikis et al., 1995; Watanabe-Fukunaga et al., 1993; Estaquier, et al., 1995; Galle, et al., 1995; Stassi et al., 1997; Dowling et al., 1996; D'Souza et al., 1996).

Based on the experimental work described below, the present invention provides in various aspects methods and means for modulating apoptosis and/or cell proliferation. Inducing apoptosis and/or inhibiting cell proliferation may be used in therapeutic contexts including proliferative disorders such as tumors, cancer and psoriasis. Inhibiting apoptosis may be used in therapeutic contexts including type I diabetes, multiple sclerosis and liver cirrhosis, and HIV infection. Tachiban et al (*Cancer Research* (1995) 55: 5528–5530) have reported correlation between progression of astrocytomas and increased expression of Fas in the tumour cells. De Maria and Testi (*Immunology Today* (1998) 19: 121–125) review evidence of cells expressing Fas and its natural ligand in the proximity of lesions in multiple sclerosis, type I diabetes, liver diseases and HIV infection.

The surprising discovery of anti-Fas autoantibodies in human serum allows for modulation of binding of those antibodies to Fas to modulate Fas-mediated effects, particularly apoptosis. Peptide fragments of Fas, and mimetics thereof, may be used to block antibody binding to Fas, inhibiting or increasing binding of Fas ligand to Fas. Prior to the work of the present inventors, it would not have been reasonable to expect administration of peptide fragments of Fas (a self-antigen) to have any utility.

As noted below in the experimental section, aspects of the present invention are exemplified by peptide fragments of Fas known as Fp5, with sequence GQFCHKPCP-PGERKARDCTV (SEQ ID NO: 1) corresponding to $Gly_{40}$-$Val_{59}$ of Fas, Fp8 with sequence QEGKEYTDKAHF-SSKCRRCR (SEQ ID NO: 2), Fp9 with sequence HFSSKCRRCRLCDEGHGLEV (SEQ ID NO: 3), Fp11, with sequence EINCTRTQNTKCRCKPNFFC (SEQ ID NO: 4), corresponding to $Glu_{100}$-$Cys_{119}$ of Fas, Fp12 with sequence KCRCKPNFFCNSTVCEHCDP (SEQ ID NO: 5), and Fp17 with sequence WLCLLLLPIPLIVWVKRKEV (SEQ ID NO: 6) corresponding to $Trp_{160}$-$Val_{179}$ of Fas, and Fp18 with sequence LIVWVKRKEVQKTCRKHRKE (SEQ ID NO: 7). Fp5 is demonstrated herein to be able to induce apoptosis. Fp8 and Fp9 comprise amino acids which are important for binding of Fas to its natural ligand, FasL.

Fp11 and Fp17 are demonstrated herein to be able to block apoptosis. Auto-antibodies against Fp11 and Fp17 induce apoptosis, so administration of these and related peptides may be used to block apoptosis of Fas carrying cells. Auto-antibodies against Fp5 may have the property of a homeostatic regulator of apoptosis by interfering with the binding of natural Fas ligand to Fas, so administration of Fp5 peptide and related peptides may be used in increase Fas ligand binding to Fas positive cells, inducing apoptosis. Auto-antibodies against Fp8 may function as a homeostatic regulator of Fas-mediated apoptosis by occupying the Fas region which is engaged in bringing to ligand. Such antibodies may be used as inducers or blockers or Fas-mediated apoptosis, depending on the state of activation of the relevant cell.

In one aspect the present invention provides a peptide which is a fragment of Fas, preferably human Fas, for use in a method of treatment of the human or animal body by therapy. The treatment may be of an individual with a complaint, disease or disorder, or may be prophylactic, as discussed further below.

Preferred peptides for use in accordance with aspects and embodiments of the present invention include the Fp5, Fp8, L10 Fp9, Fp11, Fp12, Fp17 and Fp18 peptides for which the sequences are provided herein.

Experiments show that peptide 16, which has an over lap of 10 amino acids with Fp17, has low or no reactivity with human sera. (Peptide 16 has the sequence KEEGSRSNLG-WLCLLLLPIP (SEQ ID NO: 8)). This provides indication of particular importance for the C-terminal part of Fp17. This is supported by the findings with Fp18 (see Table 1). A further embodiment of the present invention therefore provides a peptide including or consisting of the amino acid sequence QKTCRKHRKE (SEQ ID NO: 9; examples of a peptide including such sequence be ing Fp17 and Fp18).

A peptide for use in the present invention may be a fragment of Fas or may be a variant or derivative thereof, by way of addition, deletion, insertion or substitution of one or more amino acids. Such a variant or derivative thereof will generally retain ability to modulate, either induce or inhibit, apoptosis and/or cellular proliferation (e.g. as measured using Jurkat cells or T-cells).

Preferably, the amino acid sequence of a variant or derivative peptide shares sequence similarity or identity with the relevant Fas fragment sequence, preferably at least about 30%, or 40%, or 50%, or 60%, or 70%, or 75%, or 80%, or 85% similarity or identity, or at least about 90% or 95% similarity or identity. As is well-understood, similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Similarity may be as defined and determined by the TBLASTN program, of Altschul et al. (1990) *J. Mol. Biol.* 215: 403–10, which is in standard use in the art. Similarity or identity may be over the full-length of the relevant polypeptide or may more preferably be over a contiguous sequence of about 15, 20, 25, 30, 35 or 40 amino acids, compared with the relevant wild-type amino acid sequence. Default parameters are used.

A peptide according to the present invention may be provided in a fusion with additional amino acids. Additional amino acids may be fused at one or both of the N-terminus and the C-terminus of the peptide. The additional amino acids may be an amino acid sequence that is not a fragment of Fas protein, or may be an amino acid sequence that is part of that protein.

A peptide according to a further aspect of the invention may include or consist essentially of a Fas fragment. Additional amino acids may be included, which amino acids may or may not be found contiguously within Fas, and the peptide may be about 10, 15, 20, 25, 30, 35 or 40 amino acids in length. A peptide according to this aspect may be included within a larger fusion protein, particularly where the peptide is fused to a non-Fas (i.e. heterologous or foreign) sequence, such as a polypeptide or protein domain.

A peptide of the invention may be up to about 40 amino acids in length, e.g. about 10–40 amino acids in length, e.g. about 10–20.

A peptide may provided in isolated form, e.g. after its production by expression from encoding nucleic acid. As noted further below, one or more peptides in accordance with the present invention may be provided by peptide synthesis.

A plurality of peptides each with the amino acid sequence of a different selected peptide may provided in isolated form, individually or in a mixture. Different peptide fragments of Fas that are not naturally joined contiguously (or appropriate variants or derivatives thereof) may be provided joined contiguously together in peptides or polypeptides.

A further aspect of the present invention provides the Fp17 peptide, also variants and derivatives thereof that retain the ability to modulate apoptosis and/or cell (e.g. Jurkat or T-cell) proliferation.

Peptides and polypeptides (e.g. fusion molecules including a peptide as discussed) in accordance with the present invention may be made using any of a variety of techniques at the disposal of the ordinary person skilled in the art.

Peptides may be synthesized using standard peptide chemistry such as by the common method employing Fmoc (Fluorenilmetil-ossicarbonil),-Bu (tert-butil), as described in Atherton and Sheppard (1989), *Solid Phase Peptide Synthesis, a Practical Approach*, IRL Press, Oxford.

A convenient way of producing a peptide or polypeptide according to the present invention is to express nucleic acid encoding it, by use of the nucleic acid in an expression system. Accordingly, the present invention also encompasses a method of making a peptide or polypeptide (as disclosed), the method including expression from encoding nucleic acid encoding the peptide or polypeptide (generally nucleic acid according to the invention). This may conveniently be achieved by growing a host cell in culture, containing such a vector, under appropriate conditions which cause or allow expression of the polypeptide. Peptides and polypeptides may also be expressed in in vitro systems, such as reticulocyte lysate.

Polynucleotides encoding peptides and polypeptides according to the present invention represent further aspects of the invention. In one aspect there is provided a polynucleotide encoding a peptide as disclosed. In a still further aspect, a polynucleotide is provided which includes a plurality of nucleotide sequences encoding peptides or polypeptides according to the invention. This allows for production of a mixture of peptides or polypeptides in a single expression reaction.

Nucleic acid encoding a peptide or polypeptide according to the present invention may be used in nucleic acid immunization in order to modulate apoptosis and/or cell proliferation in a mammal, such as a human individual for a therapeutic or prophylactic purpose, or a non-human mammal for such a purpose or in order to produce antibodies for subsequent manipulation and/or use (e.g. in diagnostic or therapeutic contexts as discussed further below.)

Nucleic acid encoding a peptide or polypeptide according to the present invention may be used in a method of gene therapy, in modulation of apoptosis and/or cellular proliferation such as in prevention and/or treatment of a disorder in which such modulation has a beneficial effect. This requires use of suitable regulatory elements for expression and a suitable vector for deliver of the expression unit (coding sequence and regulatory elements) to host cells. A variety of vectors, both viral vectors and plasmid vectors, are known in the art, see e.g. U.S. Pat. No. 5,252,479 and WO 93/07282. In particular, a number of viruses have been used as gene transfer vectors, including papovaviruses, such as SV40, vaccinia virus, herpes viruses, including HSV and EBV, and retroviruses. Many gene therapy protocols in the prior art have used disabled murine retroviruses. A variety of adenovirus and adeno-associated viral vectors have been developed. Alternatives to viral vectors include transfer mediated by liposomes and direct DNA uptake and receptor-mediated DNA transfer.

Host cells containing nucleic acid encoding a peptide or polypeptide (or mixture thereof) according to the present invention may themselves be used in therapeutic or prophylactic treatment of individuals. Such host cells are chosen in order to target the delivery of the nucleic acid encoding the peptide to the relevant site of the body in which target lesions develop. For example, in multiple sclerosis apoptosis of Fas expressing oligodendrocytes may be mediated by an increase in anti-Fp17 auto-antibodies. Provision of Fp17 in the brain may be used to block these antibodies, and this may be achieved using host cells that home to the brain, e.g. macrophages.

Nucleic acid is generally provided as DNA or RNA, though may include one or more nucleotide analogues, and may be wholly or partially synthetic. Nucleic acid molecules and vectors according to the present invention may be provided in isolated and/or purified form, e.g. in substantially pure or homogeneous form. The term "isolate" may be used to reflect all these possibilities. Where a DNA sequence is specified, unless context requires otherwise the RNA equivalent, with U substituted for T where it occurs, is encompassed.

Where it is desired to express a peptide or polypeptide from encoding nucleic acid, the nucleic acid includes appropriate regulatory control sequences. Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 19891 Cold Spring Harbor Laboratory Press. Many known techniques and protocols for manipulation of nucleic acid, for example in preparation of nucleic acid constructs, a mutagenesis, sequencing, introduction of DNA into cells and gene expression, and analysis of proteins, are described in detail in Current Protocols in Molecular Biology, Ausubel et al. eds., John Wiley & Sons, 1992.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli*.

A further aspect of the present invention provides a host cell containing nucleic acid as disclosed herein. The nucleic acid of the invention may be integrated into the genome (e.g. chromosome) of the host cell. Integration may be promoted by inclusion of sequences which promote recombination with the genome, in accordance with standard techniques. The nucleic acid may be on an extra-chromosomal vector within the cell.

A still further aspect provides a method which includes introducing the nucleic acid into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. As an alternative, direct injection of the nucleic acid could be employed. Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded peptide or polypeptide is produced. If the peptide or polypeptide is expressed coupled to an appropriate signal leader peptide it may be secreted from the cell into the culture medium. Following production by expression, a peptide or polypeptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

A peptide or polypeptide according to the present invention may be used as an immunogen or otherwise in obtaining binding antibodies. Antibodies are useful in purification and other manipulation of polypeptides and peptides, diagnostic screening and therapeutic contexts, including passive immunization. This is discussed further below.

Particularly useful in such contexts are the Fp17 peptide and variants and derivatives thereof in a accordance with the present invention, including fragments of Fp17 including the C-terminal 10 amino acids, and variants and derivatives thereof.

According to a further aspect of the present invention there is provided a method of obtaining one or more antibody molecules containing a binding site able to bind Fas, the method including bringing into contact a population of antibody molecules and a peptide according to the present invention, and selecting one or more antibody molecules of the population able to bind said peptide.

Selected antibody molecules may be of IgG or IgM isotype.

The method may involve bringing the population of antibodies into contact with a plurality of peptides according to the invention.

The peptide or peptides may be administered to a non-human mammal to bring them into contact with a population of antibody molecules produced by the mammal's immune system, then one or more antibody molecules able to bind the peptide or peptides may be taken from the mammal, or cells producing such antibody molecules may be taken from the mammal. The mammal may be sacrificed.

If cells are taken from the mammal, antibody molecules may be taken from said cells or descendants thereof. Such descendants in particular may include hybridoma cells.

Instead or as well as immunizing an animal, a method of obtaining antibodies as disclosed may involve displaying the population of antibody molecules on the surface of bacteriophage particles, each particle containing nucleic acid encoding the antibody molecule displayed on its surface.

Nucleic acid may be taken from a bacteriophage particle displaying an antibody molecule able to bind a peptide or peptides of interest, for manipulation and/or use in production of the encoded antibody molecule or a derivative thereof (e.g. a fusion protein, a molecule including a constant region or other amino acids, and so on). Instead of using bacteriophage for display, ribosomes or polysomes may be used, e.g. as disclosed in U.S. Pat. No. 5,643,768, USA-5,658,754, WO95/11922.

Antibody molecules may be provided in isolated form, either individually or in a mixture. A plurality of antibody molecules may be provided in isolated form. Preferred antibodies according to the invention are isolated, in the sense of being free from contaminants such as antibodies able to bind other polypeptides and/or free of serum components. Monoclonal antibodies are preferred for some purposes, though polyclonal antibodies are within the scope of the present invention.

The present invention also extends to methods of obtaining and/or raising antibodies to one or more peptides or polypeptides of the invention. Such methods may include administering a peptide or polypeptide or mixture of peptides or polypeptides to a mammal in order to raise an antibody response. In a therapeutic or prophylactic context the mammal may be human or non-human. For the production of antibodies or antibody-producing cells to be isolated and used for any of a variety of purposes, a step of sacrificing a non-human mammal may be included. Such a non-human mammal may be for example mouse, rat, rabbit, dog, cat, pig, horse, donkey, goat, sheep, camel, Old World monkey, chimpanzee or other primate. Antibodies may be obtained from immunized animals using any of a variety of techniques known in the art, and screened, preferably using binding of antibody to peptide or polypeptide of interest. For instance, Western blotting techniques or immunoprecipitation may be used (Armitage et al, Nature, 357:80–82, 1992).

The production of polyclonal and monoclonal antibodies is well established in the art. Monoclonal antibodies can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB-A-2188638 or EP-A-239400. Humanized antibodies in which CDRs from a non-human source are grafted onto human framework regions, typically with the alteration of some of the framework amino acid residues, to provide antibodies which are less immunogenic than the parent non-human antibodies, are also included within the present invention. A hybridoma producing a monoclonal antibody according to the present invention may be subject to genetic mutation or other changes, which may or may not alter the binding specificity of antibodies produced. Cloning and expression of chimeric antibodies are described in EP-A-0120694 and EP-A-0125023.

As an alternative or supplement to immunising a mammal with a peptide, an antibody specific for a protein may be obtained from a recombinantly produced library of expressed immunoglobulin variable domains, e.g. using bacteriophage which display functional immunoglobulin binding domains on their surfaces—for instance see WO92/01047- or ribosomes/polysomes as noted above. The library may be naive, that is constructed from sequences obtained from an organism which has not been immunised with any of the proteins (or fragments), or may be one constructed using sequences obtained from an organism which has been exposed to the antigen of interest.

Antibodies according to the present invention may be modified in a number of ways. Thus the invention covers antibody fragments, derivatives, functional equivalents and homologues of antibodies, including synthetic molecules and molecules whose shape mimics that of an antibody enabling it to bind an antigen or epitope. Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')$_2$ fragments, a bivalent fragment including two Fab fragments linked by a disulphide bridge at the hinge region. Single chain Fv fragments are also included.

An antibody molecule according to the invention may be of the IgG or IgM isotype, and this may be preferred for certain embodiments.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

The reactivities of antibodies on a sample (e.g. in a diagnostic test) may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

One favoured mode is by covalent linkage of each antibody with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine. Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The mode of determining binding is not a feature of the present invention and those skilled in the art are able to choose a suitable mode according to their preference and general knowledge.

Antibodies according to the present invention may be used in screening for the presence of a peptide or polypeptide, for example in a test sample containing cells or cell lysate as discussed, and may be used in purifying and/or isolating a peptide or polypeptide according to the present invention, for instance following production of the polypeptide by expression from encoding nucleic acid therefor.

Antibodies are also useful in prophylaxis, by way of passive immunisation, and in therapy. Where antibodies are to be administered, it may be preferable to include a mixture of antibodies, such as antibodies collectively cross-reactive with a plurality of peptides according to the present invention.

Antibodies which bind a peptide in accordance with the present invention may themselves be used as immunogens in the production of anti-idiotypic antibodies. These may be used to mimic a peptide epitope in raising an immune response in an individual, e.g. for therapeutic and/or prophylactic purposes.

An antibody may be provided in a kit, which may include instructions for use of the antibody, e.g. in determining the presence of a particular substance in a test sample. One or more other reagents may be included, such as labelling molecules, buffer solutions, elutants and so on. Reagents may be provided within containers which protect them from the external environment, such as a sealed vial.

Antibodies against peptides (e.g. Fp17) in accordance with the present invention may be used in diagnostic contexts, for example to determine the presence in an individual, or a sample removed from an individual, of cells such as tumour cells expressing high levels of Fas. A method may involving employing an anti-Fp17 antibody (for example), contacting a test sample with the antibody and determining binding of the antibody to the sample.

The present invention also provides assay methods for compounds able to modulate apoptosis and/or cell proliferation.

Further aspects of the present invention provide the use of a peptide of the invention as disclosed, and/or encoding nucleic acid therefor, in screening or searching for and/or obtaining/identifying a substance, e.g. peptide or chemical compound, which interacts and/or binds with the peptide and/or interferes with its ability to bind antibodies directed against it, and/or modulates its ability to affect Fas-mediated apoptosis. Further aspects of the invention similarly provide use of an antibody against a peptide of the invention in screening for a substance able to modulate binding of antibody to the peptide and/or binding of antibody to Fas and/or ability of binding of antibody to Fas to induce or inhibit Fas-mediated apoptosis.

For instance, a method according to one aspect of the invention includes providing a peptide or antibody of the invention and bringing it into contact with a substance, which contact may result in binding between the peptide or antibody and the substance. Binding may be determined by any of a number of techniques available in the art, both qualitative and quantitative.

In various aspects the present invention is concerned with provision of assays for substances which inhibit interaction between a peptide of the invention and an antibody directed against it.

Further assays are for substances which interact with or bind a peptide of the invention.

One aspect of the present invention provides an assay which includes:
(a) bringing into contact a peptide according to the invention and a putative binding molecule or other test substance; and
(b) determining interaction or binding between the polypeptide or peptide and the test substance.

Another aspect of the present invention provides an assay method which includes:
(a) bringing into contact an antibody able to bind a peptide according to the invention and a putative binding molecule or other test substance; and
(b) determining interaction or binding between the antibody and the test substance.

A substance which interacts with the peptide or antibody of the invention may be isolated and/or purified, manufactured and/or used to modulate its activity as discussed.

A further aspect of the present invention provides an assay method which includes:
(a) bringing into contact a substance including a Fas fragment, mutant, variant or derivative thereof, an antibody which is able to bind the substance; and a test compound, under conditions in which in the absence of the test compound being an inhibitor, said substance and said antibody interact;
(b) determining interaction between said substance and said antibody.

Such an assay method may determine interaction between complete Fas and antibody, or a Fas fragment, such as a peptide fragment selected from Fp5, Fp8, Fp9, Fp11, Fp12, Fp17, Fp18 and the C-terminal 10 amino acids of Fp17 (N-terminal amino acids of Fp18).

Such an assay may include determination of interaction between Fas and antibody, with a peptide according to the invention also being presence, the assay determine the effect of the test substance on ability of the peptide to modulate interaction between Fas and antibody.

The precise format of an assay of the invention may be varied by those of skill in the art using routine skill and knowledge. For example, interaction between a peptide and another molecule such as an antibody may be studied in vitro by labelling one with a detectable label and bringing it into contact with the other which has been immobilised on a solid support, such as a plastic surface. Suitable detectable labels include $^{35}S$-methionine which may be incorporated into recombinantly produced peptides and polypeptides. Other labels or markers include alkaline phosphatase, peroxidase, avidin-biotin, which may be coupled directly to an anti-peptide antibody. A further option for those skilled in the art is to use a labelled anti—anti-peptide antibody which may be reacted to peptide-anti-peptide. Activity of alkaline phosphatase, peroxidase or avidin-biotin, or other label, may be measured in a spectrophotometer.

Further assays according to aspects of the present invention involve determination of the ability of a test substance to modulate Fas-mediated apoptosis of cells.

The binding of antibody to Fas, e.g. present on a cell membrane, may be inhibited by adding soluble Fas or a fragment thereof or other peptide according to the present invention. A T-cell line, such as Jurkat cells, expressing Fas on the surface may be employed. Thus, ability of a test substance to modulate apoptosis induced by an antibody directed against a peptide of the invention may be determined.

The amount of apoptosis may be determined, for instance by detecting DNA fragmentation or changes in phosphatidylserine translocation occurring at the cell membrane. DNA fragmentation may be measured using conventional agarose gel electrophoresis. Changes in phosphatidylserine translocation may be analysed by staining with labelled annexin V followed by FACS analysis.

A method of screening for a substance which modulates Fas-mediated apoptosis may include contacting one or more test substances with T-cells or other Fas positive cells and anti-Fas antibodies, particularly antibodies directed against a peptide in accordance with the invention, in a suitable reaction medium, determining the level of apoptosis and comparing that level with the level in a comparable reaction medium untreated with the test substance or substances. A difference in apoptosis between the treated and untreated reaction media is indicative of a modulating effect of the relevant test substance or substances.

Combinatorial library technology (Schultz, J S (1996) Biotechnol. Prog. 12:729–743) provides an efficient way of testing a potentially vast number of different substances for ability to modulate Fas activity. Prior to or as well as being screened for modulation of activity, test substances may be screened for ability to interact with a peptide or antibody of the invention, e.g. in a yeast two-hybrid system. This may be used as a coarse screen prior to testing a substance for actual ability to modulate Fas activity.

The amount of test substance or compound which may be added to an assay of the invention will normally be determined by trial and error depending upon the type of compound used.

Typically, from about 0.01 to 100 nM concentrations of putative inhibitor compound may be used, for example from 0.1 to 10 nM. Greater concentrations may be used when a peptide is the test substance.

Compounds which may be used may be natural or synthetic chemical compounds used in drug screening programmes. Extracts of plants which contain several characterised or uncharacterised components may also be used. Other candidate inhibitor compounds may be based on modelling the 3-dimensional structure of a polypeptide or peptide fragment and using rational drug design to provide potential inhibitor compounds with particular molecular shape, size and charge characteristics.

Following identification of a substance which modulates or affects Fas activity, the substance may be investigated further. Furthermore, it may be manufactured and/or used in preparation, i.e. manufacture or formulation, of a composition such as a medicament, pharmaceutical composition or drug. These may be administered to individuals.

Thus, the present invention extends in various aspects not only to a substance identified as a modulator of FAs activity, in accordance with what is disclosed herein, but also a pharmaceutical composition, medicament, drug or other composition comprising such a substance, a method comprising administration of such a composition to a patient, e.g. for treatment (which may include preventative treatment) of disease, use of such a substance in manufacture of a composition for administration, e.g. for treatment of disease, and a method of making a pharmaceutical composition comprising admixing such a substance with a pharmaceutically acceptable excipient, vehicle or carrier, and optionally other ingredients.

Also encompassed within the scope of the present invention are functional mimetics of peptide fragments of Fas which are able to modulate apoptosis and/or cellular proliferation. A "functional mimetic" is a substance which may not contain an active portion of the relevant amino acid sequence, and probably is not a peptide at all, but which retains the relevant activity.

Non-peptide "small molecules" are often preferred for many in vivo pharmaceutical uses. Accordingly, a mimetic or mimic of the substance (particularly if a peptide) may be designed for pharmaceutical use. The designing of mimetics to a known pharmaceutically active compound is a known approach to the development of pharmaceuticals based on a "lead" compound.

This might be desirable where the active compound is difficult or expensive to synthesize or where it is unsuitable for a particular method of administration, e.g. peptides may not be well suited as active agents for oral compositions as they may be quickly degraded by proteases in the alimentary canal. Mimetic design, synthesis and testing may be used to avoid randomly screening large number of molecules for a target property.

There are several steps commonly taken in the design of a mimetic from a compound having a given target property.

Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modeled to according its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesize, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimization or modification can then be carried out to arrive at one or more final mimetics for in vivo or clinical testing.

Further aspects of the present invention therefore relate to provision of non-peptidyl mimetics of peptides for use in the present invention. One aspect of the invention provides the use of a peptide as disclosed in the identification or design of a non-peptidyl mimetic which retains ability to modulate apoptosis and/or cell proliferation. A further aspect provides a method of testing a non-peptidyl mimetic of a peptide for use in the present invention for ability to modulate apoptosis and/or cellular proliferation.

As noted already, peptides, mimetics, polypeptides, antibodies and nucleic acid in accordance with the present invention may be formulated into compositions, and are useful in pharmaceutical contexts. These compositions may include, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A peptide may be linked to an appropriate carrier. Various methods of coupling peptides to other molecules are known in the art, including disulphide forming reagents (where the peptide includes a cysteine—or a cysteine is added to the peptide for this purpose), thio-ether forming coupling agents and so on. Carriers include human serum albumin (HSA), tetanus toxoid, other rather large proteins that have reasonable half-lives under physiological conditions, and stable non-proteinaceous molecules such as polysaccharides and copolymers of amino acids.

An adjuvant may be included, such as alum, oil-in-water emulsions or Freund's Adjuvant (Complete or Incomplete). Cytokines may be used to potentiate immunogenicity of the peptide or polypeptide composition.

Whether it is a polypeptide, antibody, peptide, nucleic acid molecule, mimetic, small molecule or other pharmaceutically useful compound according to the present invention that is to be given to an individual, administration may be in a "prophylactically effective amount" or a "therapeutically effective amount" (as the case may be, although prophylaxis may be considered therapy). Most preferably the effect is sufficient to prevent the individual from suffering one or more clinical symptoms, and/or reduce pain. A therapeutic effect is sufficient to potentiate the immune response of an individual to pre-existing disorder, preferably sufficient to antagonise the disorder, wholly or partially. Most preferably the effect is sufficient to ameliorate one or more clinical symptoms, and/or cure the disorder and/or reduce pain in the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

Further aspects of the invention provide methods of treatment including administration of a peptide, mixture of peptides, antibody molecule or mixture of antibody molecules, as provided, pharmaceutical compositions including such a peptide, mixture of peptides, antibody molecule or mixture of antibody molecules, and use of such a peptide, mixture of peptides, antibody molecule or mixture of antibody molecules, in the manufacture of a medicament for administration, for example in a method of making a medicament or pharmaceutical composition including formulating the specific binding member with a pharmaceutically acceptable excipient. Nucleic acid encoding peptides or polypeptides, and non-peptide mimetics may be employed.

A composition may be administered alone or in combination with other treatments, either simultaneously or sequentially dependent upon the condition to be treated and the availability of alternative or additional treatments. In some embodiments of the present invention the relevant molecule is used in conjunction with anti-CD3 antibodies or other anti-CD3 binding molecules.

One aspect of the present invention provides use of a peptide as disclosed in the manufacture of a medicament for use in a method of treatment of the human or animal body by therapy. Treatment may be of a proliferative disorder, such as a tumour, cancer or psoriasis, or an autoimmune disorder, type diabetes, multiple sclerosis, liver cirrhosis and so on. Apoptosis may be induced or inhibited and/or cellular proliferation inhibited or stimulated.

Another aspect provides a method of treating a mammal against such a disorder, the method including administering a peptide or mixture of peptides, mimetic or mimetics, antibody or antibodies or nucleic acid as disclosed, to the mammal.

A peptide, antibody or other therapeutic molecule according to the present invention may be targeted to a lesion, e.g. tumour. Antibodies diffuse rather well through tissues and injection at a site distal to that of the lesion may be employed. Alternatively, direct injection into a lesion, e.g. tumour, may be employed, and this may be utilised for peptides and other molecules. Targeted viral vectors may be used to deliver nucleic acid encoding a peptide, polypeptide or antibody according to the invention to a site for expression of the encoded product.

Further aspects and embodiments of the present invention will be apparent to those skilled in the art based on the present disclosure. Embodiments of and experimental basis for the present invention will now be described in more detail with reference to the following figures:

FIG. 1 illustrates results of experiments demonstrating that sera from healthy blood donors contain antibodies against human Fas peptides. Serum specimens from 30 individuals were analyzed. ELISA titers of antibodies against the reactive Fas peptides Fp5, Fp11 and Fp17 are expressed as percentiles and median values by use of the box (notched) and whisker plot of the StatView+Graphics statistical computer program.

EXPERIMENTAL

Figure 1:
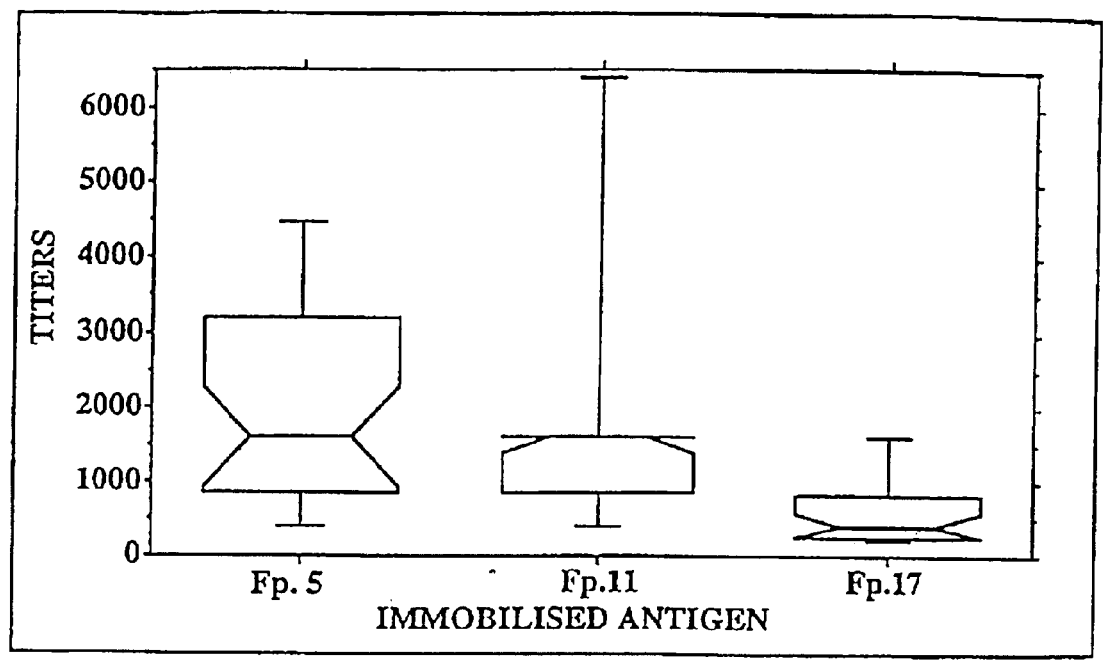

Synthesis of Fas peptides.

The derived amino acid sequence (a.a.1–179) of the Fas protein (Itoh et al., 1991) was used for simultaneous multiple solid-phase peptide synthesis (Houghten et al, 1985) of 20 amino acid long peptides (with a 10-residue overlap).

The peptides demonstrated 70–97% homogeneity, as revealed by HPLC. These peptides were used in ELISA of 30 human sera obtained from healthy blood donors and the specificity of the assay was confirmed by peptide competition ELISA as described (Leonov et al., 1994). Peptides Fp5 ($Gly_{40}$-$Val_{59}$), Fp11 ($Glu_{100}$-$Cys_{119}$), and Fp17 ($Trp_{160}$-$Val_{179}$) were selected as positively reacting with human sera and were used in subsequent experiments.

Purification and Characterization of Fas Autoantibodies.

Affinity columns were made by coupling 7 mg each of Fp5, Fp11, and Fp17 to ECH-Sepharose (Pharmacia Biotech, Sweden) with N-ethyl-N'-(3-dimethyaminopropyl) carbodiimide hydrochloride, as described in the manufacturer's affinity chromatography protocol. After overnight absorption of pooled human sera of healthy blood donors, the anti-peptide antibodies were eluted by 4 M KSCN, concentrated, dialyzed and sterilized by filtration through 0.22 μm pore size filter. These eluates were analyzed by electrophoresis and Western Blot using NOVEX NUPAGE Gel kit: 10% Bis-Tris Gels/MOPS SDS Buffers according to manufacturer's protocols (NOVEX, San Diego, Calif.). Purified human IgG and mouse IgM, and NOVEX Mark 121 Wide Range Protein Standard were used as reference.

Solubilized proteins from 10 Jurkat leukemia T cells were separated and transferred to 0.45 μm pore size supported nitrocellulose membrane (Bio-Rad Laboratories AB, Sweden) using NOVEX Western Blot buffer system. Membranes were probed by IgM class anti-Fas mAb CH-ll (Medical Biological Laboratory, Nagoya, Japan) and IgG1 class anti-Fas mAb clone 13 (Transduction Laboratories, Lexington, Ky.) according to manufacturer's recommendations; human control IgG (not reacting with Fas peptides), eluates from affinity columns, pooled human sera before and after column immunoadsorption diluted by 1/50 in PBS containing 5% non-fat dry milk, 0.1% Tween-20 and 0.001% anti-foam agent (Sigma).

Bound antibodies were revealed by sequential use of F(ab)$_2$ fragments of goat anti-human light chain antibodies conjugated with peroxidase and SuperSignal ULTRA chemiluminescent substrate system (both are from Pierce, Rockford, Ill.).

Detection of Apoptosis

Jurkat leukemia T cells (2×10$^6$/well) in RPMI 1640 supplemented with 10% FCS, 10 mM-HEPES, 2 mM-glutamin, 50 FM-2-mercaptoethanol, 0.1 M-nonessential amino acids, and 10 µg/ml gentamicin (RPMI-HEPES) were cultured in 24-well plates previously coated overnight with anti-Fas peptide antibodies isolated by affinity-column. The antibody-concentrations were anti-Fp5 (10 µg/ml), anti-Fp11 (10 µg/ml) and anti-Fp17 (40 µg/ml). Cells were collected after 48 h incubation, and the fragmented DNA of apoptotic cells was assessed by Apoptosis Detection System, Fluorescein (Promega, Madison, Wis.) based on TdT-mediated dUTP Nick-End Labeling (TUNEL) assay and FACS analysis (CellQuest software, Becton Dickinson) according to manufacturer's instructions. For apoptosis inhibition experiments, Jurkat cell culture medium was supplemented with 200 ng/ml of recombinant Fas-Fc chimera (R&D Systems Europe Ltd, Abingdon, UK). Inhibition of CH-11-mediated apoptosis was performed as described in Fadeel et al., 1997. Data are presented as the mean value of four independent experiments, and the standard error of mean is indicated by the error bars.

Proliferation Assay.

PBMC were stimulated with phytohemagglutinin (PHA) (10/g/ml) (Pharmacia Biotech, Sweden) for 48 hours. Approximately 5×10$^5$ stimulated cells were then cultured in a flat-bottom 96-well plate previously coated overnight with anti-Fas peptide affinity isolated antibodies and purified anti-CD3 (OKT-3, 10 µg/ml) in RPMI-HEPES medium. After 48 hours incubation, the proliferation was assessed by Alamar Blue Assay (Biosource International, USA.) and the results were expressed as percent difference in reduction of (fluorometric/colorometric) REDOX indicator between antibody coated and control (without antibodies) wells according to manufacturer's instructions (AMS Biotechnology AB, Sweden).

The FasL expression in PHA-stimulated T-cell blasts was detected at the same time point by use of IgG1 anti-FasL mAb, clone 33 (Transduction Laboratories, Lexington, Ky.) and Phycoerythrine (PE) conjugated F(ab)$_2$ fragments of goat anti-mouse IgG (Dako, Sweden). Results were expressed as percent of positive cells analyzed by FACS. Non-Stimulated PBMC were Isolated by Ficoll-Hypaque (Pharmacia Biotech, Sweden) and used for proliferation assays as described above for PHA stimulated cells. Apoptosis was quantified by TUNEL assay and expressed as percent difference in fluorescence between antibody containing and antibody-free cultures.

Computer-Modelling of Fas

The molecular model for the extracellular domain (Itoh et al., 1991) of the Fas monomer (amino acids His$_{38}$-Lys$_{149}$) was created using knowledge-based protein modeling methods as implemented in the Swiss-Model server (Peitsch et al., 1995 and 1996). The model was based on the three-dimensional structure of the TNFR1 (entry No. 1TNR in Brookhaven Protein Data Bank).

Results

Anti-Fas Antibodies of IgG Class are Present in the Serum of Blood Donors.

Peptides corresponding to the extracellular and transmembrane parts of human Fas (Itoh, et al., 1991) were synthesized. Three of these peptides, Fp5 (Gly$_{40}$-Val$_{59}$ with sequence GQFCHKPCPPGERKARDCTV, SEQ ID NO: 1), Fp11 (Glu$_{100}$-Cys$_{119}$ with sequence EINCTRTQNT-KCRCKPNFFC. SEQ ID NO: 4) and Fp17 (Trp$_{160}$-Val$_{179}$ with sequence WLCLLLLPIPLIVWVKRXEV, SEQUENCE ID NO: 6), were reactive with antibodies present in the blood of the 30 healthy donors (FIG. 1). The serum titers against the three different peptides were variable with the lowest mean titers detected against Fp17.

These antibodies were purified by affinity chromatography based on immobilized Fas peptides. Polyacrylamide gel electrophoresis (PAGE) analysis of the eluates demonstrated that the majority of purified proteins had a molecular weight corresponding to IgG class antibodies. The specificity of the isolated antibodies was further assayed by Western blot with whole Fas protein which confirmed that anti-Fas antibodies are present in the serum of healthy human subjects.

Similar experiments were performed with commercially available immunoglobulin preparations derived from pooled human serum enriched by immunosorbence for immunoglobulin fractions (Gammagard-Baxter, Hyland, Glendale, Calif. USA).

Results for the experiments with human serum and with the immunoglobulin preparations are shown in Table 1.

The presence of both IgG and IgM auto-antibodies was established.

Autoantibodies to Fas regions represented by Fp11 and Fp17 mediate apoptosis of Jurkat leukemia cells through Pas.

Figure 2A:
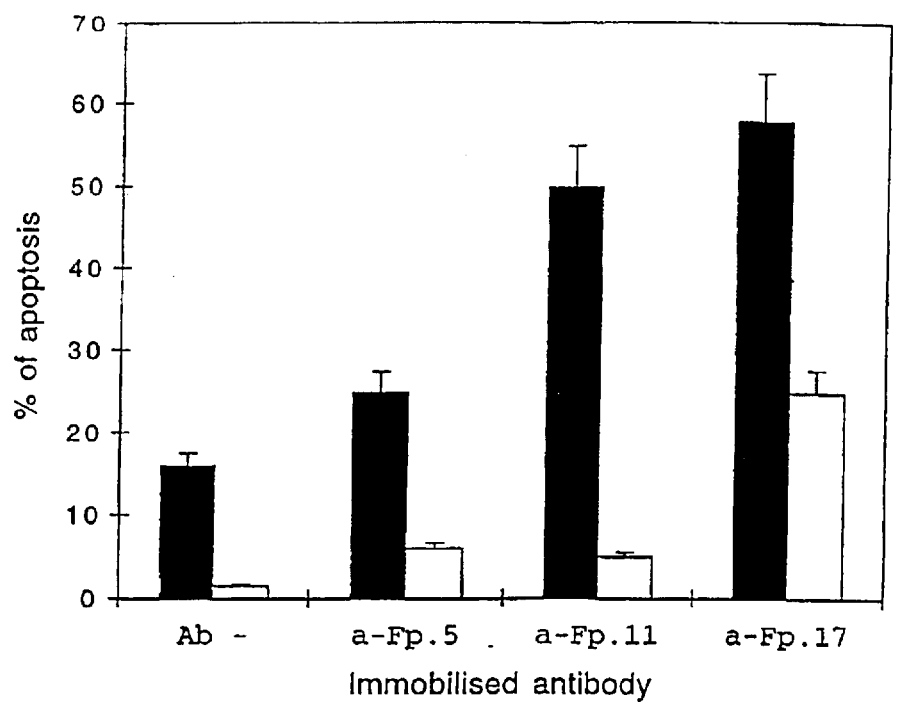
FIG. 2(A) shows results of TUNEL assay of apoptosis of Jurkat leukemia T cells in absence (filled) and in presence (open) of Fas-Fc chimeric protein demonstrating that anti-Fas peptide auto-antibodies can induce Fas-mediated apoptosis.

Ability to mediate apoptosis and inhibition of proliferation was determined using antibodies immobilized to plastic surface. Immobilized human antibodies directed to Fp11 and Fp17 induced apoptosis in respectively 49% and 58% of Jurkat leukemia cells (FIG. 2(A)). The level of apoptosis induced by Fp5 did not differ significantly from control well in which antibodies were not included, 25% versus 18%.

Next, ability of anti-Fas autoantibodies to affect cell proliferation in the Jurkat cell system was analysed. Human antibodies directed to Fp17 inhibited cell proliferation by 40% as compared to control well; the levels of inhibition of proliferation were lower for anti-Fp5 and anti-Fp11, 8% and 10% respectively. The use of either protein A or anti-human Ig immunosorbent to immobilize the anti-peptide antibodies gave similar results. Thus, IgG class anti-Fas peptide antibodies present in human blood can induce apoptosis and inhibit proliferation in Jurkat T cells. Without being bound by any particular theory, this biological effect is likely to be mediated through cross-linking of Fas molecules on the cell surface, a mechanism suggested to operate for anti-Fas monoclonal antibodies of both IgM and IgG subclasses, including IgG1 (Dhein et al., 1992; Fadeel et al., 1997).

Two sets of blocking experiments were performed to establish that apoptosis induced by anti-Fas autoantibodies is mediated through Fas.

The chimeric protein Fas-Fc, consisting of the extracellular part of Fas (aa 1–173) and Fc-part of human IgG was previously shown to block apoptosis caused by Fas-FasL interaction (Itoh et al., 1991). Addition of this protein to Jurkat cells completely reduced apoptosis induced by human antibodies to Fp5 and Fp11 (FIG. 2(A)). For Jurkat cells incubated with anti-Fp17, the reduction of apoptosis was 60%, although it can be noted that the portion of Fas included in the Fas-Fc fragment is 1–173 whereas Fp$_{117}$ span is between Trp$_{160}$ snd Val$_{179}$.

Figure 2B:
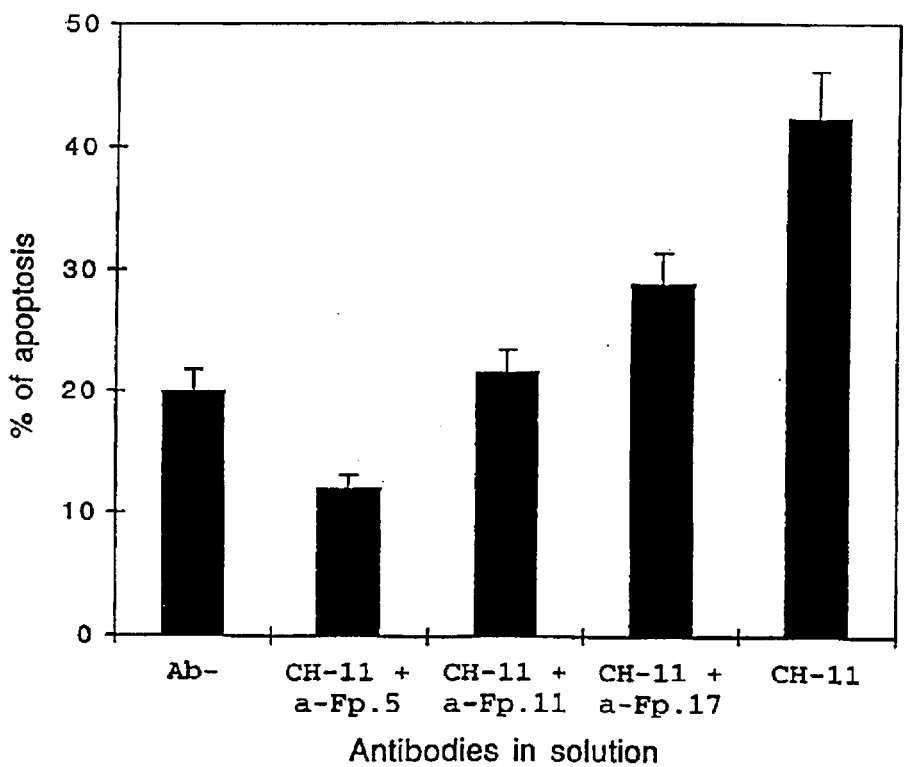
FIG. 2(B) shows that anti-Fas peptide auto-antibodies can inhibit apoptosis induced by CH-11 murine anti-Fas antibodies.

In the second set of experiments purified anti-Pas autoantibodies in soluble form were used to block apoptosis induced by the anti-Fas IgM monoclonal CH-11. Anti-Fas IgG1 murine monoclonal antibodies were previously demonstrated to inhibit the effect of CH-11 (Fadeel et al., 1997). The autoantibodies directed to Fp-5 and Fp-11 reduced CH-11-mediated apoptosis by more than 50%, thus to levels similar to the spontaneous apoptosis occurring in the non-treated cells. Human auto-antibodies to Fp-17 only diminished the CH-11 induced apoptosis by 31% (FIG. 2(B)). It has previously been shown that Fp11 can block the apoptotic activity of CH-11 (Fadeel et al., 1995). Thus, the reduction of apoptosis noticed upon incubation with anti-Fp11 is probably due to a specific blocking of the Fas site recognized by CH-11. Antibodies binding to Fp5 and Fp17 of Fas, on the other hand, may sterically hinder binding of CH-11.

Together, these data demonstrate that apoptosis of immortalized Jurkat leukemia T cells induced by human anti-Fas autoantibodies is mediated through a Fas-dependent pathway.

Co-stimulation with Anti-CD3 Antibodies and Anti-Fas Autoantibodies Affects Proliferation According to the State of Cell-Activation.

Next, ability of human anti-Fas peptide autoantibodies to affect proliferation of primary T cells was investigated.

Cross-linking of CD3/TCR receptor is known to trigger a Fas-dependent process termed activation-induced cell death (AICD) and reduced cell proliferation (Varadhachary et al., 1997; Dhein et al., 1995; Brunner, et al., 1997; Ju et al., 1997).

Figure 3A:
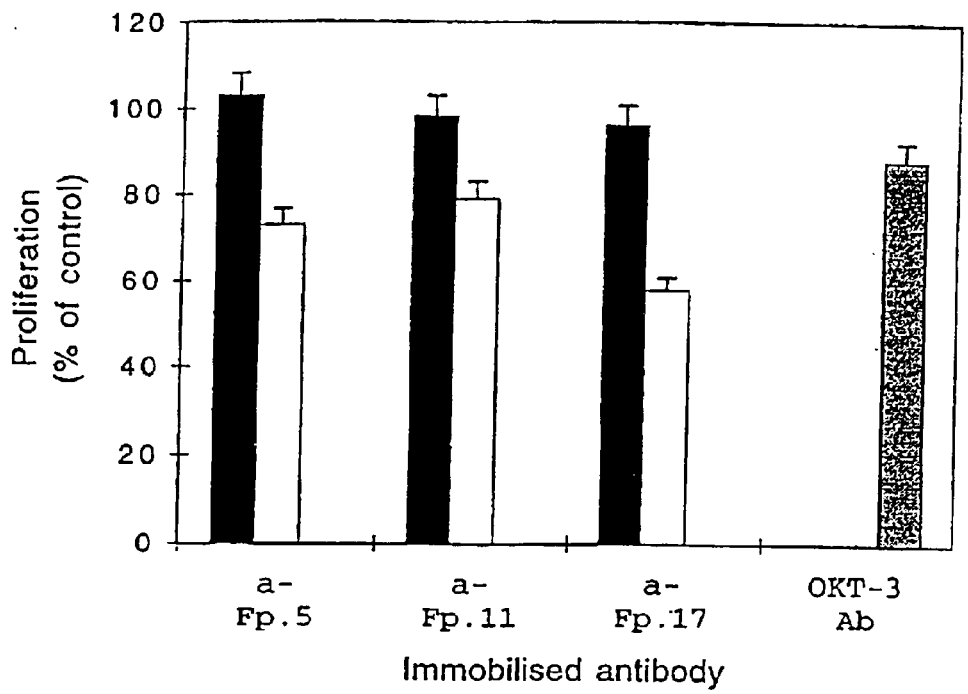
FIG. 3(A) shows proliferation of T-cell blasts in response to stimulation with anti-Fas peptide autoantibodies in absence (filled) or presence (open) of immobilized anti-CD3 mob. The gray bar represents the result of the anti-CD3 mAb alone.

PHA-stimulated T cell blasts were incubated with the isolated anti-Fas antibodies together with antibodies directed to CD3. The auto-antibodies had no effect when immobilized alone (FIG. 3(A)). However, costimulation of cells with immobilized anti-CD3 antibodies and anti-Fas autoantibodies significantly reduced proliferation (21–42% reduction) in comparison with anti-CD3 alone (12% reduction). Anti-Fas autoantibodies can therefore enhance CD3-mediated anti-proliferative effect.

Figure 3B:
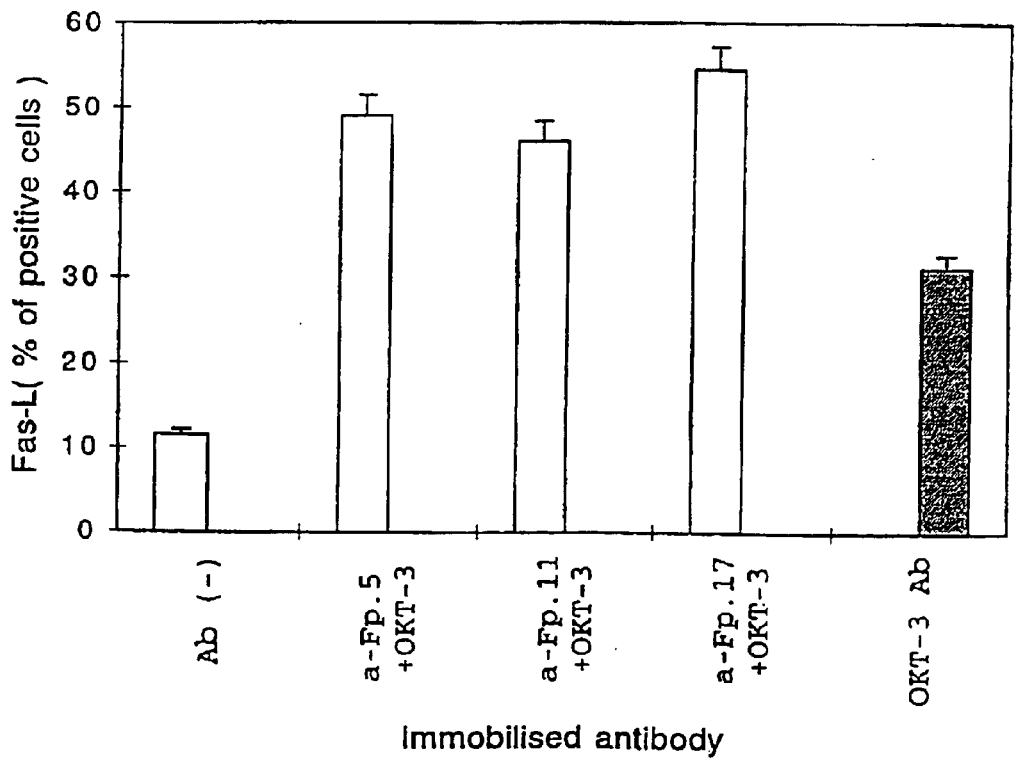
FIG. 3(B) shows FasL expression on the surface of PHA-activated T-cell blasts in response to stimulation with anti-10 Fas peptide autoantibodies in absence (filled) or presence (open) of immobilized anti-CD3 mAb. The gray bar represents the result of the anti-CD3 mAb alone.

Interestingly, it was found that reduction of proliferation was paralleled with increased expression of FasL (FIG. 3(B)). The data suggest that costimulation of the CD3/TCR complex and Fas by anti-CD3 and human anti-Fas autoantibodies might decrease the proliferation of activated T cell blasts. A possible mediator of this effect may be FasL, as demonstrated by up-regulation of this molecule upon cross-linking of Fas and CD3.

Figure 4A:
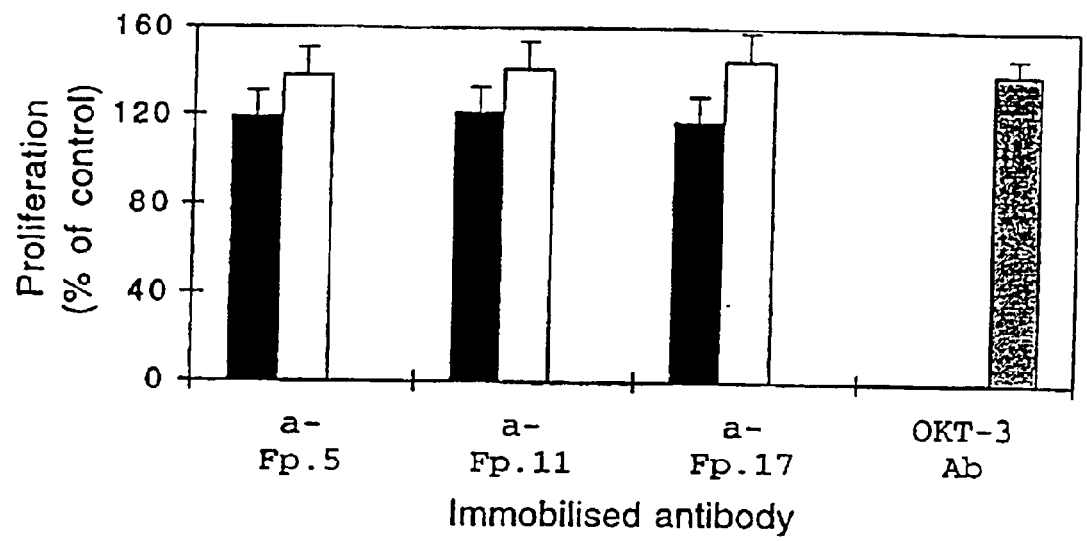
FIG. 4(A) shows proliferation of non-stimulated PBMC in response to stimulation with anti-Fas peptide autoantibodies in absence (filled) or presence (open) of anti-CD3 mAb.
Figure 4B:
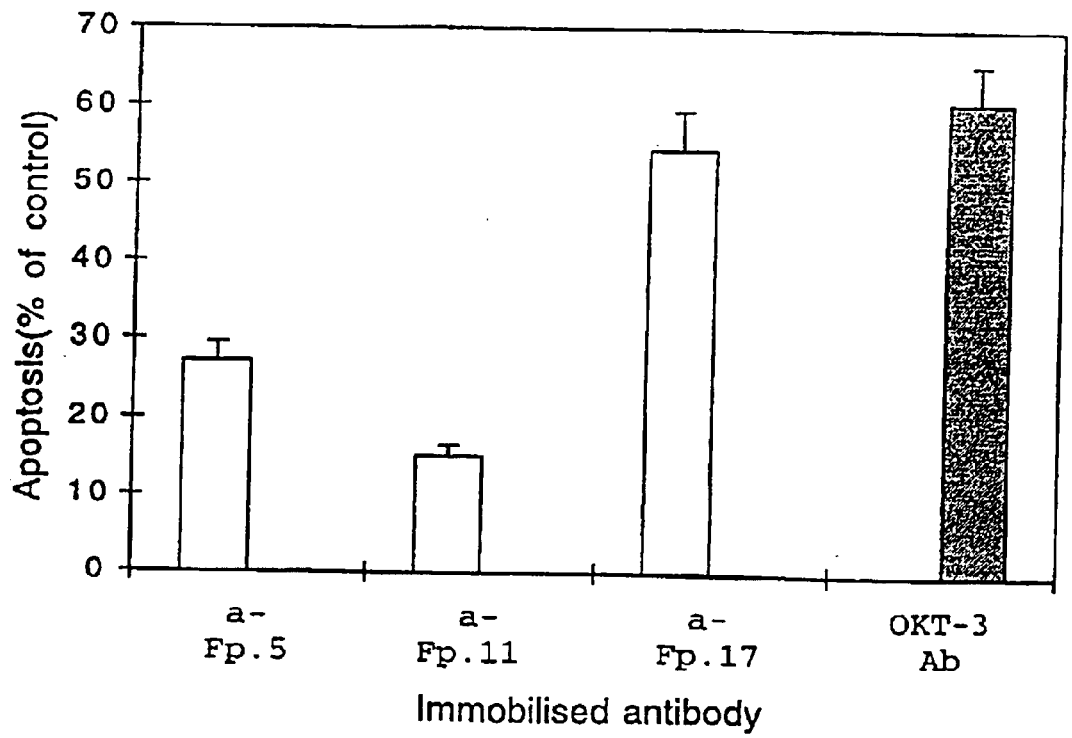
FIG. 4(B) shows apoptosis of non-stimulated PBMC in response to stimulation with anti-Fas peptide autoantibodies in absence (filled) or presence (open) of anti-CD3 mAb.

CD3/TCR and Fas engagement in cellular proliferation and apoptosis was further investigated in experiments with non-stimulated peripheral blood mononuclear cells (PBMC). In this system immobilized human anti-Fas auto-antibodies alone or in combination with anti-CD3 increased proliferation between 20 and 40% (FIG. 4(A)). This effect may be due to reduction of spontaneous apoptosis. Indeed, the costimulation with anti-CD3 antibody and human anti-Fas auto-antibodies induced reduction of spontaneous apoptosis by 15 to 55% for the three anti-peptide antibodies (FIG. 4(B)). These data correlate with previous observations that CD3 and Fas costimulation using murine monoclonal antibodies induced increase of proliferation of isolated T cells (Alderson et al., 1993; Alderson et al., 1994).

Thus, human anti-Fas auto-antibodies can modulate the biological effect of CD3/TCR ligation in non-stimulated PBMC through a mechanism including reduction of apoptosis.

Pas-binding Sites for Autoantibodies and Fas L.

To gain knowledge on how anti-Fas autoantibodies may induce apoptotic/activation signals through Fas, a molecular model of this protein was created where the antibody-binding sites could be visualized in relation to the surfaces of FasL interaction. The extracellular part of the Fas molecule has distinct sequence homology to TNF receptor 1 (TNFR1; Nagata and Golstein, 1995). Based on the three-dimensional structure of TNFR1 a molecular model (Peitsch, 1995 and 1996) of Fas was created.

The model shows that antibody binding to the Fas regions represented by Fp5 ($Gly_{40}$-$Val_{59}$) and Fp11 ($Glu_{100}$-$Cys_{119}$) may sterically interfere with FasL binding to $Arg_{86}$ and $Arg_{87}$, amino acids that are critical for Fas-FasL binding (Starling, et al., 1997). This may also be relevant for amino acids $Lys_{84}$, $Leu_{90}$, $Glu_{93}$ and $His_{126}$, that are thought to be important for Pas-FasL interactions (Starling, et al., 1997). Thus, the localization of these two antibody-binding regions of the Fas molecule may explain the biological effect of the anti-Fas autoantibodies on cells by either interference with FasL binding or by direct induction of apoptotic or proliferative signals. In this context it is important to note that the apoptotic activity of the prototypic anti-human Fas mAb (clone CH-11) depends on binding to the region represented by Fp11, thus indicating that this segment display pronounced antigenic property (Fadeel et al., 1995). Of course performance of aspects of the present invention does not require knowledge of how the invention works and the scope of the invention is not limited by any particular theory.

The region of Fas represented by Fp17 ($Trp_{160}$-$Val_{119}$) is predicted to be a transmembrane domain and could not be included in the model. The recognition of this Fas domain by auto-antibodies mediating biological effect indicates that part of this domain is likely to be exposed on the cell surface. The titers against Fp17 were the lowest among the three peptides. However, the apoptosis-inducing effect of these anti Fp17 antibodies was evident and exceeded that of anti-Fp5 and anti Fp11 when used at the same concentration.

Fp17 does not contain residues involved in the contact with FasL. The results provide indication that autoantibody binding to this Fp17 region may efficiently transduce a signal to the intracellular cell death machinery.

Discussion

The experimental work described above demonstrates the existence of biologically active human autoantibodies against Fas, one of the key molecules in the control of lymphocyte expansion/deletion in vivo (Lynch et al., 1995). The anti-Fas autoantibodies were present in the serum of a majority of healthy individuals.

The work also demonstrates that human anti-Fas autoantibodies can trigger cellular responses through the Fas receptor in vitro. This provides indication that in addition to already described modes of regulation of Fas-mediated signals (Suda et al., 1993; Irmler et al., 1997) autoantibodies constitute an additional level of modulation of Fas-mediated functions in vivo.

Paralleling previous findings on murine monoclonal antibodies (Owen-Schaub et al., 1992; Klas et al., 1993; Alderson et al., 1993 and 1994), the human autoantibodies against Fas may be used to provide both apoptosis inducing and stimulatory effects depending on the activation state of the cells. Conversion of Fas-mediated signals from cell activation to apoptosis may represent a safety mechanism by which the immune system eliminates transformed cells from the host (Alderson et al., 1994). Considering that antibodies can easily diffuse to tissues, hypothetical roles for the anti-Fas autoantibodies may be found in this balance of cell activation and apoptosis, in the termination of ongoing immune responses through AICD (Kabelitz et al., 1993) and in the maintenance of peripheral tolerance (Fisher et al., 1995; Rieux-Laucat et al., 1995).

The activity of anti-Fas autoantibodies has potential implications in diseases which are linked to Fas dysregulation, e.g. liver damage (Galle et al., 1995), insulin-dependent diabetes mellitus (Stassi et al., 1997) and multiple sclerosis (Dowling et al., 1996; D'Souza et al., 1996). Increased levels of Fas and FasL in these diseases may be paralleled by changes in the levels of Fas autoantibodies.

Autoantibodies to the three regions of Fas display different biological activity. Anti Fp17 autoantibodies are efficient in mediating apoptosis of Jurkat cells whereas anti Fp5 antibodies were found to be poor inducers of apoptosis but can efficiently block the apoptotic activity of anti-fas mAbCH-11. Thus the binding of autoantibodies to regions of Fas which may interfere spacially with the ligand (Fp5) or directly transduce apoptotic signals (Fp17) may be exploited in therapeutical settings aimed at inducing or reducing Fas-mediated apoptosis.

Measurement of distribution and titres of antibodies directed to Fas peptides in accordance with the present invention provides further insight into Fas dysregulation and involvement in pathogenesis of diseases. Such distribution and titres are measured in sera obtained from patients with multiple sclerosis, type I diabetes and HIV infection, using techniques available to those skilled in the art.

Fragments and variants of peptides of the invention which retain ability to inhibit or induce apoptosis are identified, along with minimal epitopes for binding of anti-Fas antibodies, using systematic substitution in the peptides of each individual amino acid, for instance using alanine scanning. Reactivity of human sera is evaluated with enzyme linked immunosorbent assay to define amino acids important or necessary for binding.

Colon carcinoma, hepatocellular and other carcinomas in which the expression of Fas is down-regulated (Walker et al. (1997) J. Immunology 158: 4521–4524) are treated with peptides of the invention, particularly Fp17, the C-terminal amino acids of Fp17, and fragments and variants thereof. The portion of Fas including Fp17 includes the membrane spanning peptide and may be used to provide down-stream signalling to cells to undergo apoptosis.

Antibodies against Fp17 are injected into animals to induce apoptosis of animal tumours.

Animal models representative of (i) multiple sclerosis and (ii) type I diabetes are treated with a peptide or antibody of the invention in order to block anti-Fas auto-antibody triggering of apoptosis in diseased organs.

REFERENCES

Alderson, et al. (1993). J. Exp. Med.178(6), 2231–5.
Alderson, et al. (1994). Int. Immunol. 6(11), 1799–806.
Brunner, et al. (1995). Nature 373, 441–44.
Dhein, et al. (1992). J Immunol 149(10), 3166–73
Dhein, et al. (1995). Nature 373,438–41.
Dowling, et al. (1996). J Exp Med 184(4), 1513–8.
D'Souza, et al. (1996). J Exp Med 184 (6), 2361–70.
Ellis and Atkinson, (1996). Nature Medicine 2 (2), 148–53.
Estaquier, et al. (1995). J. Exp. Med. 182(6), 1759–67.
Fadeel, et al. (1995). Int. Immunol 12(7), 1967–1975.
Fadeel, et al. (1997). Int. Immunol 9(2), 201–9.
Fisher, et al. (1995). Cell 81, 935–46.
Galle, et al. (1995). J. Exp. Med. 182(5), 1223–30.
Houghten, R. A. (1985). PNAS 82(15), 5131–5.
Irmler, et al. (1977). Nature 388, 190–5.
Itoh, et al. (1991). Cell, 66(2), 233–43.
Ju, et al. (1995). Nature 373, 444–48.
Kabelitz, et al. (1993). Immunol. Today 14(7), 338–9.
Katsikis, et al. (1995). J. Exp. Med. 181(6), 2029–36.
Klas, et al. (1993). Int. Immunol. 5(6), 625–30.
Leonov, et al. (1994). J. Gen. Virol. 75, 1353–9.
Lutomski, et al. (1995). J Neuroimmunol 57(1–2), 9–15.
Lynch, et al. (1995). Immunol Today 16(12), 569–74.
Mapara, et al. (1993) Eur. J. Immunol. 23(3), 702–8.
Nagata and Golstein (1995). Science 267, 1449–56.
Ogasawara, et al. (1993). Nature 364, 806–9.
Owen-Schaub, et al. (1992). Cell. Immunol. 140(1), 197–205.
Peitsch, M. C. (1995). Bio/Technology, 13, 658–660.
Peitsch, M. C. (1996). Biochem Soc Trans, 24, 274–9.
Prabhakar, et al. (1997). Immunol Today 18 (9), 437–42.
Rieux-Laucat, et al. (1995). Science 268,1347–9.
Rose and Bona (1993). Immunol Today 14 (9), 426–30.
Silvestris, et al. (1996). J. Exp. Med. 184(6), 2287–300.
Smith, et al. (1994). Cell, 76(6), 959–62.
Song, et al. (1996). Immunol Today, 17 (5), 232–38.
Starling, et al. (1977). J. Exp. Med. 185(8), 1487–92.
Stassi, et al. (1997). J Exp Med 186(8), 1193–200.
Suda, et al. (1993). Cell 75(6), 1169–78.
Trauth, et al. (1989). Science 245, 301–5.
Varadhachary, et al. (1997). P.N.A.S. Usa 94(11), 5778–83.
Vassilev, et al. (1996). Scand J Immunol 44(5), 535–9.
Watanabe-Fukunaga, et al. (1992). Nature 356, 314–7.
Weis, et al. (1995). Experimental Cell Research 219(2), 699–708.
Yonehara, et al. (1989). J. Exp. Med. 169(5), 1747–56.

All documents mentioned anywhere herein are incorporated by reference.

TABLE 1

Reactivity of human serum and immunoglobulin preparations to Fas peptides in ELISA.

| Peptide number | Human serum | Immunoglobulin preparations (Gammagard) |
|---|---|---|
| Fp1 | – | – |
| Fp2 | – | – |
| Fp3 | – | – |
| Fp4 | – | – |
| Fp5 | ++ | + |
| Fp6 | – | – |
| Fp7 | – | – |
| Fp8 | – | +++ |
| Fp9 | – | ++ |
| Fp10 | – | – |
| Fp11 | +++ | +++ |
| Fp12 | ++ | ++ |
| Fp13 | – | – |
| Fp14 | – | – |
| Fp15 | – | – |
| Fp16 | – | + |
| Fp17 | +++ | + |
| Fp18 | not done | +++ |

+ = <0.5 O.D. 490 nm;
++ = <1.0 O.D.;
+++ > 1.0 O.D.

What is claimed is:

1. A method of obtaining one or more human antibody molecules containing a binding site that binds human Fas, the method comprising bringing into contact a population of human antibody molecules and a peptide of 10–20 amino acids in length which is a fragment of human Fas, said fragment comprising an amino acid sequence selected from the group consisting of:

(i) GQFCHKPCPPGERKARDCTV (SEQ ID NO. 1),
(ii) QEGKEYTDKAHFSSKCRRCR (SEQ ID NO. 2),
(iii) HFSSKCRRCRLCDEGHGLEV (SEQ ID NO. 3),
(iv) EINCTRTQNTKCRCKPNFFC (SEQ ID NO. 4),
(v) KCRCKPNFFCNSTVCEHCDP (SEQ ID NO. 5),
(vi) WLCLLLLPIPLIVWVKRKEV (SEQ ID NO. 6),
(vii) LIVWVKRKEVQKTCRKHRKE (SEQ ID NO. 7), and
(viii) QKTCRKHRKE (SEQ ID NO. 9);

said fragment comprising an immunogenic amino acid sequence which is found within an amino acid sequence selected from said group; and selecting one or more human antibody molecules able to bind said peptide.

2. A method of according to claim 1 wherein an antibody molecule directed to said peptide, or a mixture of antibody molecules directed to one or more said peptides, is obtained and is formulated into a composition comprising pharmaceutically acceptable excipient, carrier, buffer or stabiliser.

3. A method according to claim 1 further comprising providing host cells in vitro that produce the selected human antibody molecules able to bind said peptide.

4. A method according to claim 3 wherein an antibody molecule directed to said peptide, or a mixture of antibody molecules directed at least one of said peptides, is obtained and is formulated into a composition comprising a pharmaceutically acceptable excipient, carrier, buffer or stabiliser.

\* \* \* \* \*

SEQUENCE LISTING

<160> NUMBER OF SEQ ID NOS: 9

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 1

Gly Gln Phe Cys His Lys Pro Cys Pro Pro Gly Glu Arg Lys Ala Arg
 1               5                  10                  15

Asp Cys Thr Val
            20

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 2

Gln Glu Gly Lys Glu Tyr Thr Asp Lys Ala His Phe Ser Ser Lys Cys
 1               5                  10                  15

Arg Arg Cys Arg
            20

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 3

His Phe Ser Ser Lys Cys Arg Arg Cys Arg Leu Cys Asp Glu Gly His
 1               5                  10                  15

Gly Leu Glu Val
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 4

Glu Ile Asn Cys Thr Arg Thr Gln Asn Thr Lys Cys Arg Cys Lys Pro
 1               5                  10                  15

Asn Phe Phe Cys
            20

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic -continued

```
      sequence

<400> SEQUENCE: 5

Lys Cys Arg Cys Lys Pro Asn Phe Phe Cys Asn Ser Thr Val Cys Glu
 1               5                  10                  15

His Cys Asp Pro
            20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 6

Trp Leu Cys Leu Leu Leu Pro Ile Pro Leu Ile Val Trp Val Lys
 1               5                  10                  15

Arg Lys Glu Val
            20

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 7

Leu Ile Val Trp Val Lys Arg Lys Glu Val Gln Lys Thr Cys Arg Lys
 1               5                  10                  15

His Arg Lys Glu
            20

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 8

Lys Glu Glu Gly Ser Arg Ser Asn Leu Gly Trp Leu Cys Leu Leu Leu
 1               5                  10                  15

Leu Pro Ile Pro
            20

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 9

Gln Lys Thr Cys Arg Lys His Arg Lys Glu
 1               5                  10
```